(12) United States Patent
Harks et al.

(10) Patent No.: US 10,383,687 B2
(45) Date of Patent: Aug. 20, 2019

(54) COMBINED ABLATION AND ULTRASOUND IMAGING

(75) Inventors: Godefridus Antonius Harks, Eindhoven (NL); Szabolcs Deladi, Eindhoven (NL); Jan Frederik Suijver, Eindhoven (NL); Maya Ella Barley, Eindhoven (NL); Edwin Gerardus Johannus Maria Bongers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 359 days.

(21) Appl. No.: 13/576,022

(22) PCT Filed: Feb. 3, 2011

(86) PCT No.: PCT/IB2011/050462
§ 371 (c)(1),
(2), (4) Date: Jul. 30, 2012

(87) PCT Pub. No.: WO2011/095937
PCT Pub. Date: Aug. 11, 2011

(65) Prior Publication Data
US 2012/0302877 A1    Nov. 29, 2012

(30) Foreign Application Priority Data
Feb. 5, 2010 (EP) .................................. 10152815

(51) Int. Cl.
*A61B 18/18* (2006.01)
*A61B 18/04* (2006.01)
(Continued)

(52) U.S. Cl.
CPC .............. *A61B 18/18* (2013.01); *A61B 18/04* (2013.01); *A61B 18/1492* (2013.01);
(Continued)

(58) Field of Classification Search
None
See application file for complete search history.

(56) References Cited

U.S. PATENT DOCUMENTS 5,246,436 A * 9/1993 Rowe .................. A61F 9/00802
604/20
5,529,766 A 6/1996 Klaveness et al.
(Continued)

FOREIGN PATENT DOCUMENTS

WO 2008017990 A1 2/2008
WO 2008017992 A2 2/2008

OTHER PUBLICATIONS

N.F. Marrouche et al., "Phase-Array Intracardiac Echocardiography Monitoring During Pulmonary Vein Isolation in Pateints With Atrial Fibrillation: Impact on Outcome and Complications", 2003; Downloaded from http://circ.ahajournals.org/cgi/content/full/107/21/2710. pp. 2710-2716.
(Continued)

*Primary Examiner* — Mark D Remaly

(57) ABSTRACT

The present invention relates to a system (100) for combined ablation and ultrasound imaging of associated tissue (40), which is particularly useful for use in an ablation process. The system comprises an interventional device (20) with an ultrasound transducer and an ablation unit. During an ablation process, the interventional device (20) can be applied for both ablation and imaging of the tissue (40) subject to the ablation. A controlling unit (CTRL) is further comprised within the system, and arranged to calculate a predictor value based on one or more signals from the ultrasound transducer, where the predictor value relates to a risk of impending tissue damage due to a rapid release of bubble energy. According to a specific embodiment, a primary
(Continued)

signal is sent if the predictor value exceeds a threshold value, so that proper measures can be taken.

16 Claims, 5 Drawing Sheets

(51) Int. Cl.
*A61B 18/14* (2006.01)
*A61B 17/34* (2006.01)
*A61B 18/12* (2006.01)
*A61B 18/20* (2006.01)
*A61B 18/24* (2006.01)
*A61B 17/00* (2006.01)
*A61B 18/00* (2006.01)
*A61B 90/00* (2016.01)

(52) U.S. Cl.
CPC ....... *A61B 17/3478* (2013.01); *A61B 18/1206* (2013.01); *A61B 18/1477* (2013.01); *A61B 18/1815* (2013.01); *A61B 18/20* (2013.01); *A61B 18/24* (2013.01); *A61B 2017/00106* (2013.01); *A61B 2018/00029* (2013.01); *A61B 2018/00351* (2013.01); *A61B 2018/00642* (2013.01); *A61B 2018/00666* (2013.01); *A61B 2018/00875* (2013.01); *A61B 2018/1425* (2013.01); *A61B 2018/1861* (2013.01); *A61B 2018/1869* (2013.01); *A61B 2090/064* (2016.02); *A61B 2090/3784* (2016.02); *A61B 2218/002* (2013.01)

(56) References Cited

U.S. PATENT DOCUMENTS

| | | | |
|---|---|---|---|
| 6,709,432 | B2 | 3/2004 | Ferek-Patric |
| 7,025,765 | B2 | 4/2006 | Balbierz et al. |
| 7,918,850 | B2 | 4/2011 | Govari et al. |
| 8,414,508 | B2 * | 4/2013 | Thapliyal et al. ............... 601/2 |
| 8,512,250 | B2 | 8/2013 | Quistgaard |
| 8,607,800 | B2 | 12/2013 | Thapliyal et al. |
| 2005/0283074 | A1 | 12/2005 | Jackson et al. |
| 2008/0154257 | A1 | 6/2008 | Sharareh et al. |
| 2009/0030412 | A1 * | 1/2009 | Willis ............... A61B 1/00089 600/104 |
| 2009/0287205 | A1 | 11/2009 | Ingle |
| 2010/0168571 | A1 * | 7/2010 | Savery et al. ............... 600/439 |

OTHER PUBLICATIONS

P. Kotini et al.; Detection Microbubble Formation During Radiofrequency Ablation Using Phonocardiography, The European Society of Cardiology 2006, pp. 333-335.

S. Garrean et al., "Ultrasound Monitoring of a Novel Microwave Ablation (MWA) Device in Porcine Observed on Ablative Effects Near Major Intrahepatic Vessels", Accepted; Sep. 18, 2008/ Published online: Oct. 21, 2008, The Society of the Alimentary Tract. p. 1.

\* cited by examiner

COMBINED ABLATION AND ULTRASOUND IMAGING

FIELD OF THE INVENTION

The present invention relates to the field of interventional devices and control units, and more specifically to a system and method for combined ablation and ultrasound imaging.

BACKGROUND OF THE INVENTION

Ablation, such as ablation using a catheter, is a minimally invasive procedure. In this procedure, cardiac tissue is locally affected in order to block undesired conduction pathways. This can be achieved by hyperthermia using e.g. radio frequency (RF) as energy source. Upon energy delivery, a lesion starts to grow through the depth of the tissue wall, which becomes non-conducting scar tissue. Electrophysiologists aim to create lesions that run completely through the tissue wall (i.e. transmural) and are permanent (i.e. coagulated tissue, no recovery possible).

Tissue ablation is not without risk. One or more bubbles may form in the tissue during ablation, and rapid release of bubble energy can be induced.

If the tissue temperature rises rapidly, intramural evaporation may occur and a gas bubble may develop within the tissue under the electrode. Continuous application of RF energy will cause the bubble to expand and its pressure to increase, which may lead to eruption of the gas bubble through the weakest path, leaving behind a gaping hole. The release of the gas bubble is associated with a popping sound and, likely, with tearing of cardiac tissue.

In the following, such rapid release of bubble energy is referred to as a so-called "pop" or a "tissue pop". This is associated with severe complications, such as tamponades in case of cardiac ablation, and clinicians try to avoid formation of such pops.

The reference 'Detection of microbubble formation during radiofrequency ablation using phonocardiography', published in Europace (2006), 8, 333-335, discloses that characteristic acoustic signatures are present before pops and correspond to microbubble (MB) formation. However, the ability to record acoustic sounds of MB formation in vivo is not known and may be complicated by respiratory, cardiac, and muscle artefacts.

Hence, there is the need for a solution that overcomes the aforementioned disadvantages and provides a safer ablation process; this would prevent injury during ablation procedures.

SUMMARY OF THE INVENTION

The present invention preferably seeks to alleviate or eliminate the above-mentioned disadvantages of during an ablation process. In particular, it may be seen as an object of the present invention to provide a system for ablation and ultrasound imaging which is able to calculate a predictor value, where the predictor value relates to a risk of impending tissue damage due to a rapid release of bubble energy.

It is a further object of the present invention to provide an alternative to the prior art.

Thus, the above described object and several other objects are intended to be obtained in a first aspect of the invention by providing a system for combined ablation and ultrasound imaging of associated tissue, the system comprising:

an interventional device, the interventional device comprising, an ultrasound transducer, and
an ablation unit, and
a controlling unit being operably connected to the interventional device, the controlling unit being arranged to
send a control signal to the ultrasound transducer,
receive a response signal from the ultrasound transducer, the response signal being indicative of the presence of one or more bubbles within said associated tissue, and
calculate a predictor value, where the predictor value relates to a risk of an impending tissue damage due to a rapid release of a bubble energy.

The invention is particularly, but not exclusively, advantageous for obtaining a safer ablation process. Electrophysiologists have indicated that it is extremely valuable to predict so-called "pops" or "tissue pops". Ablation may induce formation of one or more bubbles in the tissue during ablation, and this may lead to potentially harmful and rapid release of bubble energy. In the following, such rapid release of bubble energy is referred to as a so-called "pop" or a "tissue pop". A prediction of an impending pop, or a knowledge of a risk of an impending tissue damage due to a rapid release of a bubble energy, may allow relevant parameters to be properly regulated in order to prevent the pop. It is expected that this would significantly increase the safety of ablation procedures. Another advantage might be that the invention devises an integrated and miniaturized device which enables safe ablation.

Previously, acoustic signatures relating to bubbles were measured, however, these acoustic signatures related to bubbles that were formed at the interface between electrode and tissue, which is imaged by Intra Cardiac Echography (ICE). Gas formation at the interface can be caused by local heating of the fluid around the tip electrode, and does not necessarily relate to gas formation within the tissue. Moreover, the ability to record acoustic sounds of microbubble formation at this interface may be complicated in a closed-chest procedure and may require the integration of a bulky microphone in a catheter.

The ultrasound transducer in the interventional device of the present invention is preferably applied for monitoring or imaging the local cardiac tissue, the ablation process in said cardiac tissue or parameters related, directly or indirectly, to the ablation process. For example, the formation of microbubbles within the associated tissue might be monitored.

It is contemplated that the invention according to the 1$^{st}$ aspect may alternatively be implemented not using the indication of one or more bubbles within the associated tissue, but other characteristics in tissue. Such other parameters might include the local expansion of the associated tissue.

In the context of the present invention, monitoring is to be construed broadly. It includes both 1D monitoring, i.e. detecting reflected intensities along the line of sight as well as 2D imaging where an array of transducers are applied to generate a 2D image as well as time resolved imaging (so-called ultrasound "M-mode" imaging). In principle also 3D imaging may be obtained. In interventional device based monitoring, such as catheter based monitoring, it is presently normal to use (time resolved) 1D or 2D monitoring due to space constraints in the distal end region, i.e. in the tip region.

As used herein, the term "ablation" refers to any kind of suitable ablation within the teaching and general principle of the present invention. Thus, it could be radio frequency (RF) based (incl. microwave), optically based (e.g., an optical emitter, such as a laser, such as a laser emitting wavelengths in the infrared, visible or ultraviolet range), a heating element, such as a hot water balloon, or ultrasound-based ablation such as high intensity focused ultrasound (HIFU).

In the context of the present application, the term "ablation unit" refers to an optical emitter, such as a laser in case of optical-based ablation, an electrode (or other suitable RF emitting devices) in case of RF- and microwave-based ablation and to an ultrasound transducer, such as a high intensity focused ultrasound (HIFU) transducer, in case of ultrasound based ablation.

It is understood that the interventional device might be a unit wherein the ablation unit and the ultrasound transducer are integrated, however, it might also be embodied as an interventional device where the ablation unit and the ultrasound transducer are separate units. The interventional device might comprise a catheter, a needle, a biopsy needle, guidewire, sheath, or an endoscope.

The ultrasonic signal might be a pulsed-echo signal. The pulsed-echo technique is defined as sending a short ultrasound pulse by a low-Q transducer into a medium, and receiving the reflections back at the transducer from irregularities in the medium (due to change of acoustical impedance). The transit time from the initial pulse transmission to reception of the echo is proportional to the depth at which the irregularities are found.

The controlling unit may be any unit capable of sending an output signal, such as a control signal to the ultrasound transducer, and capable of receiving an input signal, such as a response signal from the ultrasound transducer, and further capable of calculating a value, such as a predictor value. The controlling unit can be implemented by means of hardware, such as electronic components such as transistors, operational amplifiers and similar components. It may, however, also be implanted as software, firmware or any combination of these, running on a processor.

The predictor value is understood to be a value representative of a risk of impending tissue damage due to a rapid release of a bubble energy. The predictor value may be a probability of impending tissue damage due to a rapid release of a bubble energy, but it may also be a parameter, such as a measurable parameter, such as a number of bubbles, such as a volume of bubbles, such as a rate of change of the number of bubbles, which may be relevant for calculating the risk of impending tissue damage due to a rapid release of a bubble energy.

In another embodiment, the controlling unit is further arranged to send a primary signal (RS) if the predictor value exceeds a threshold value (TV).

The threshold may be a number set by a user or automatically set by an apparatus, for use in comparison with the predictor value. The threshold may vary, or may be constant. In some embodiments of the invention it may always be held at a value which is always exceeded by the predictor value.

The primary signal is a signal which is sent from the controlling unit, and may be an analogue signal, such as a voltage or a digital signal. It may also be other forms of signals, such as an acoustic signal, such as an audible signal. It may also be an optical signal such as a visible signal. The primary signal may have a constant value or it may be varied.

An advantage of sending a primary signal if the predictor value exceeds a threshold value (TV), might be that the primary signal can be received by another unit, such as an alarm unit, such as a loudspeaker or a lamp, such as a flashlight. Alternatively, the primary signal can be read of by personnel carrying out or monitoring the ablation, whom might be able to adjust parameters related to the ablation in a proper manner.

According to yet another embodiment of the invention, the primary signal (RS) is arranged to regulate a parameter related to the ablation.

An advantage of this embodiment might be, that the primary signal can be received by another unit, such as any other unit controlling parameters relevant for ablation, may be any other unit controlling any one of the ablation unit, irrigation flow, a contact force applied between the interventional device and the associated tissue, and a position of the ablation unit, and that this other unit can be adjusted in a proper manner.

According to a further embodiment of the invention, the threshold value is a function of any one of: ablation power (which is understood to be a power emitted from the ablation unit in order to dissipate power in the associated tissue), the previous history of the response signal, a measured contact force between the interventional device and the associated tissue, an electrical impedance of the associated tissue, a structure of the associated tissue, a duration of the ablation, the ability of the associated tissue to exchange heat with the surroundings, a temperature of the associated tissue, the temperature of the ablation electrode and the irrigation flow rate at the electrode tip.

An advantage of having the threshold value being a function of other parameters is that the threshold can then be adjusted in order to have an optimal value. In an exemplary embodiment, the threshold value is adjusted in response to a previous development of the formation of bubbles in the tissue so that a rapid change in the formation of bubbles within the tissue might entail a relatively low threshold, whereas a slow development of the formation of bubbles might entail a higher threshold. The ability of the associated tissue to exchange heat with the surroundings might be affected by various factors, e.g., the tissue might have a larger or smaller surface area through which heat can be exchanged with the surroundings, and the surroundings may be more or less heat conductive.

In another embodiment, the controlling unit is arranged to vary the primary signal depending on the value of the predictor value.

In a simple example the ablation unit, such as an RF generator that is used in many ablation procedures, can be installed such that it automatically switches off in case it receives a primary signal. In this case, the primary signal can be constant or varying depending on the predictor value. However, in other examples, it is advantageous to instead vary other relevant parameters, such as the energy dissipated in the tissue during ablation, so as to sustain the ablation process. An advantage of this might be that it enables a more controlled and optimized ablation process. Another advantage might be that the ablation process can be adjusted so as to apply sufficient energy to create transmural lesions while maintaining a controlled, low risk of tissue pops. There is a delicate balance for the ablation settings to be used in terms of ablation power, duration, irrigation flow, such that a transmural lesion is created without pop formation. These settings may differ for the different anatomical positions (e.g. related to blood flow and wall thickness) and may depend on the contact force.

In yet another embodiment, the controlling unit is arranged to form part of a feedback circuit. This is advantageous in order to realize an ablation process which may be automated, easily controlled and/or optimized.

In a further embodiment, the ultrasound transducer is disposed behind or in an irrigation hole of the interventional device, so as to allow an irrigation fluid to flow out of the irrigation hole, and so as to allow transmitting and/or receiving an ultrasonic signal through the irrigation hole.

It may be seen as an advantage that by placing the ultrasound transducer behind or in the irrigation hole there is no need for an acoustically transparent window. The benefit is a better signal-to-noise ratio and an increased dynamical range due to the elimination of reflection and attenuation caused by the acoustical window. Specifically, the second-order and higher-order reflections from the acoustic window (so-called ultrasonic reverberations) are completely avoided. This is a major improvement that permits to avoid substantial post-processing due to the fact that these reverberations usually show up overlapping the relevant cardiac structures in the ultrasound data.

In the context of the present application, the term "in" refers to the displacement of the ultrasound transducer within the irrigation hole itself, whereas the term "behind" refers to any position inside the distal tip which is not within the irrigation hole and which permits to the ultrasonic signals generated from the ultrasound transducer to flow through the irrigation hole undisturbed or with minimal interference from the distal tip. In particular, this may also imply that the ultrasound transducer may be able to direct its ultrasonic signals towards the irrigation hole from any displacement.

In a still further embodiment, the at least one ultrasound transducer is arranged for emitting ultrasonic signals having a frequency sufficiently high in order to detect one or more bubbles in the associated tissue. The axial resolution corresponds to the ability to resolve reflecting boundaries closely spaced in the axial direction of the transducer. Axial resolution is ~$Qc/4f$, where Q is quality factor, c is speed of sound in medium, and f is frequency of resonance. Since low Q is associated with reduction of acoustic output power, it cannot be lowered too much. Anyway, for pulsed echo imaging the Q of the transducers is kept low. The other parameter to improve axial resolution is the frequency. The gain by increasing the frequency is much more important for improving axial resolution than further reducing the Q factor. There is a trade-off between penetration depth, axial resolution and quality factor of the transducer. In one embodiment, the frequency is above 10 MHz. An advantage of choosing the frequency according to this embodiment might be that it is better for enabling the response to be able to be indicative of the creation of one or more bubbles, such as one or more small bubbles. In another embodiment, the frequency is above 20 MHz, such as within 20-25 MHz. This just covers the thickness of the heart wall no matter of position, and gives sufficiently good axial resolution.

In another embodiment, the ablation unit comprises any one of: a heating element, a radio frequency electrode, an ultrasound transducer, and a laser.

In yet another embodiment, the system comprising any one of the following devices: an electrode capable of serving as an electrode for measuring electrical impedance, a force sensor capable of measuring a contact force applied between the interventional device and the associated tissue, a temperature sensor and a localization sensor.

A possible advantage of having such a device comprised within the system is that it enables the measurement of parameters which can be advantageous to monitor and/or control, such as parameters servings as input parameter or output parameter in a feedback circuit, according to an embodiment of the present invention. The temperature sensor may be any type of thermometer, including contact thermometers or non-contact thermometers, such as thermometers based on detection of infrared radiation.

In another embodiment, the primary signal is controlling or at least having an influence on any one of the following entities: the ablation unit, irrigation flow, a contact force applied between the interventional device and the associated tissue, and a position of the ablation unit.

A possible advantage of having such entities controlled by the controlling unit is that it enables the measurement of parameters which can be advantageous to control or regulate, such as entities which are relevant parameters in controlling the ablation process.

According to a second aspect of the invention, there is presented a method for assessing a risk of impending tissue damage due to a rapid release of bubble energy, the method comprising the steps of emitting a primary ultrasonic signal into a tissue, and receiving a secondary ultrasonic signal from within the tissue, and determining if one or more bubbles are formed within the tissue, based upon information derived from the secondary ultrasonic signal, and sending the information derived from the secondary ultrasonic signal to a processor, and calculating a predictor value based on information derived from the secondary ultrasonic signal, where the predictor value relates to a risk of impending tissue damage due to a rapid release of bubble energy.

This aspect of the invention is particularly, but not exclusively, advantageous in that the method according to the present invention may be implemented into available equipment. Furthermore, the method may be implemented into an automated process. Furthermore, as the method yields a predictor value, it provides a basis for decisions regarding the ablation process.

It is understood, that the step of emitting a primary ultrasonic signal, such as an ultrasonic wave, into a tissue may be carried out using an ultrasound transducer, and similarly the step of receiving a secondary ultrasonic signal, such as an ultrasonic wave, from within the tissue, such as reflected by the tissue, may be carried out using an ultrasonic transducer.

In another embodiment according to the invention, the method further comprises the step of outputting a primary signal based upon the predictor value.

This enables the predictor value to be used quantitatively, such as in a feedback system.

According to a third aspect of the invention, the invention relates to use of a system for combined ablation and ultrasound imaging of associated tissue according to the first aspect of the invention, for controlling an ablation process.

According to a fourth aspect of the invention, there is presented a computer program product being adapted to enable a computer system comprising at least one computer having data storage means associated therewith to operate a processor arranged for receiving information derived from a secondary ultrasonic signal, and calculating a predictor value based on information derived from the secondary ultrasonic signal, where the predictor value relates to a risk of impending tissue damage due to a rapid release of bubble energy.

Such computer program product could, for example, comprise a processor running an algorithm where input parameters could comprise parameters related to bubble formation, as well as other parameters, such as ablation power, the previous history of the response signal, a measured contact force between the interventional device and the associated tissue, an electrical impedance of the associated tissue, a structure of the associated tissue, a duration of the ablation, the ability of the associated tissue to exchange heat with the surroundings, a temperature of the associated tissue, and where the output parameters could include a primary signal, such as a primary signal controlling any one of: the ablation unit, such as ablation power, irrigation flow, a contact force applied between the interventional device and the associated tissue, a position of the ablation unit.

In one embodiment, the secondary ultrasonic signal is a pulse-echo ultrasonic signal.

The first, second, third and fourth aspect of the present invention may each be combined with any of the other aspects. These and other aspects of the invention will be apparent from and elucidated with reference to the embodiments described hereinafter.

BRIEF DESCRIPTION OF THE FIGURES

The system and method for ablation and ultrasound imaging according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Embodiments of the present invention are disclosed in the following.

Figure 1:
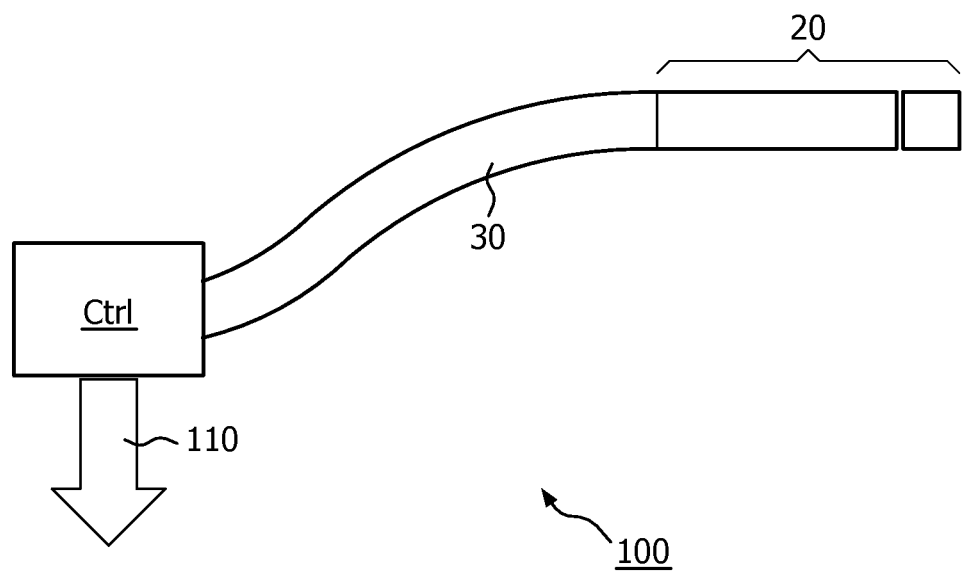
FIG. 1 shows a system for ablation and ultrasound imaging according to an embodiment of the invention.

FIG. 1 shows a general system 100 for performing ablation, the system comprising a controllable energy source for providing energy to the ablation unit and/or the ultrasonic transducer (neither shown in this figure). Additionally, a sample arm 30 is coupled to the energy source, the sample arm having at its distal end an interventional device 20 according to an embodiment of the present invention. The interventional device may include any one of the non-exhaustive list comprising a catheter, a needle, a biopsy needle or an endoscope. It is also contemplated that a plurality of ultrasound transducers could be comprised within the interventional device, and some ultrasound transducers could be only emitting whereas other transducers could be only receiving. The system 100 further comprises a controlling unit (CTRL), that is in some embodiments arranged to send a primary signal 110 if a predictor value exceeds a threshold value.

The invention might be used in tissue imaging during use, for example in connection with heart arrhythmias or in oncology, where it is advantageous to assess a risk of impending tissue damage due to a rapid release of bubble energy and thus form a basis for deciding how to operate the ablation unit. Particularly, the invention may assist in optimizing the ablation process, e.g., by forming part of a feedback circuit ensuring optimal conditions during ablation. The condition during ablation may be a function of a number of parameters including ablation power, temperature, an irrigation flow, contact force between the interventional device and the associated tissue, and the position of the ablation unit with respect to the tissue which is subject to the ablation.

Figure 2:
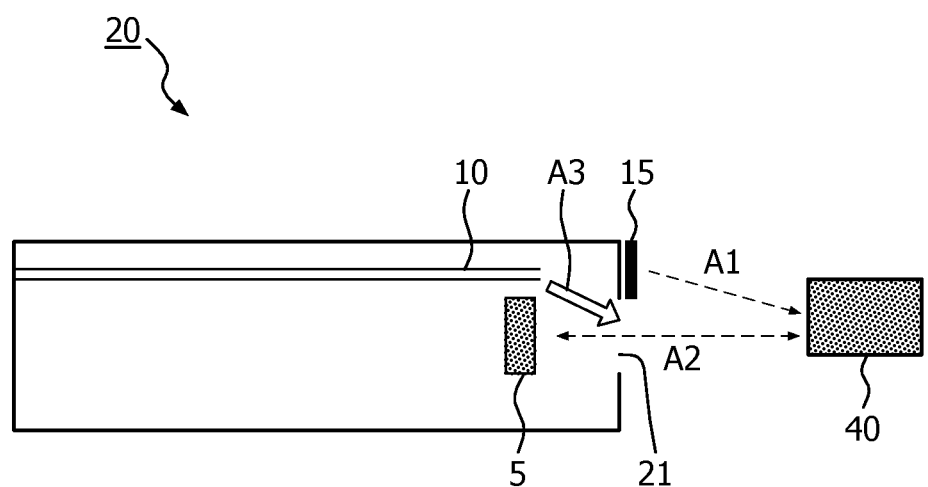
FIG. 2 shows an interventional device according to an embodiment of the invention.

FIG. 2 shows a schematic, cross-sectional drawing of an interventional device 20, in the particular figure, the interventional device is a catheter adapted for open-loop irrigated ablation of a tissue 40. However, it is to be understood that the interventional device also could also be other types of interventional devices, such as a needle or the like. The catheter 20 is adapted for open-loop irrigated ablation, e.g. RF ablation, of a tissue 40, the catheter 20 having a distal tip 22, i.e. the right-hand part of the shown catheter embraced by the bracket, where the distal tip comprises an ablation entity 15 adapted for performing ablation of the tissue 40. Note that although in FIG. 2 the ablation entity is depicted as covering only the right side of the catheter, it may also cover other of the catheter's sides. The radiation for performing ablation is schematically shown by dotted arrow A1. The required wiring for energizing and/or controlling the ablation entity is not shown in this figure for clarity. In addition, an irrigation hole 21 is provided. The irrigation fluid is flowing out of a dedicated irrigation fluid conduct 10, e.g. a flexible tube, as indicated schematically by solid arrow A3. The irrigation fluid is functioning as an acoustic coupling medium, which may be defined as a medium substantially transparent to ultrasonic signals, such as a saline solution or water or other similar liquids available to the skilled person implementing this embodiment of the invention.

Further, an ultrasound transducer 5 is positioned in the distal tip, the transducer being adapted for transmitting and/or receiving ultrasonic signals as schematically indicated by double-headed dotted arrow A2 in FIG. 2. According to an embodiment of the invention, the ultrasound transducer is disposed behind (as in this figure) or in the irrigation hole 21 of the catheter 20, so as to allow an irrigation fluid A3 to flow out of the irrigation hole, and so as to allow transmitting and/or receiving the ultrasonic signals through the same irrigation hole 21.

Advantageously, the catheter 20 may be used for open-loop irrigated radio frequency (RF) ablation.

In particular embodiments, the catheter may be a catheter with a platinum ring electrode or a catheter with an acoustically transparent foil, such as a Polymethylpentene (TPX) foil, such as a Polymethylpentene (TPX) foil coated with a metal layer for ablation. The acoustically transparent window has to mediate the contact between the catheter and the tissue, and the outside of it should be coated with a very thin (e.g. 150 nm) of conductive layer, in order to allow RF ablation. The acoustically transparent window therefore should have significantly similar acoustic impedance compared with the irrigation fluid (which is mediating the contact between the ultrasound transducer and the inner face of the acoustic window), and similar acoustic impedance as the blood or tissue that is encountered by the outside of the acoustic window in order to avoid acoustic power loss due to reflection from the interfaces. We identified materials that would be appropriate for this purpose, including Polymethylpentene (TPX) Z=1.73 [MRayls] and Pebax 4033 Z=1.67 [MRayls] or 5533 Z=1.75 [MRayls]. Blood has Z=1.68 [MRayls].

Figure 3:
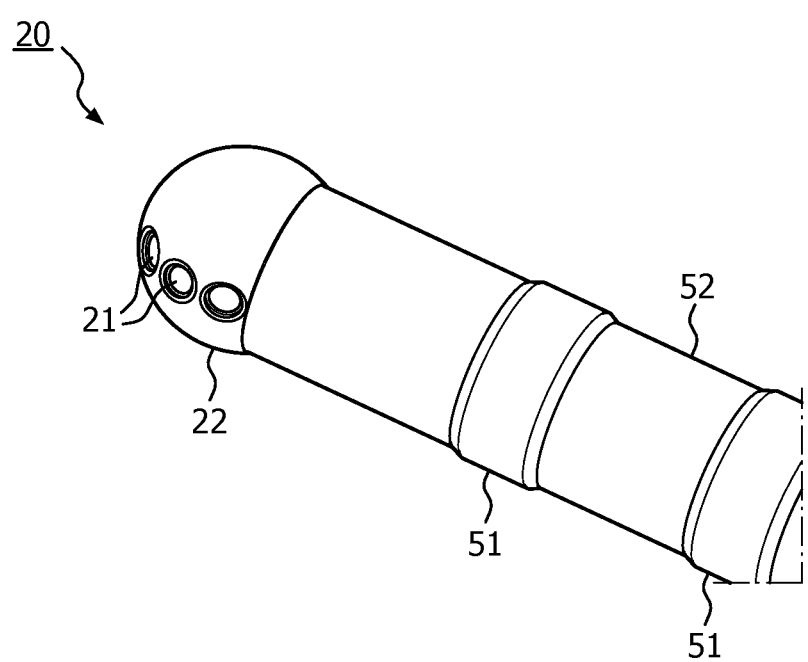
FIG. 3 shows a perspective view of a catheter according to an embodiment of the invention.

FIG. 3 shows a perspective view of a catheter 20 suitable for use as an interventional device according to an embodiment of the present invention. The tip 22 of the catheter is mounted on a flexible tube 52 for easy manipulation through the human body. Additional ring shaped electrodes 51 on the tube can measure properties like resistance and temperature. The tube 52 will contain the needed wires for addressing the transducers and will supply the irrigation liquid.

Figure 4:
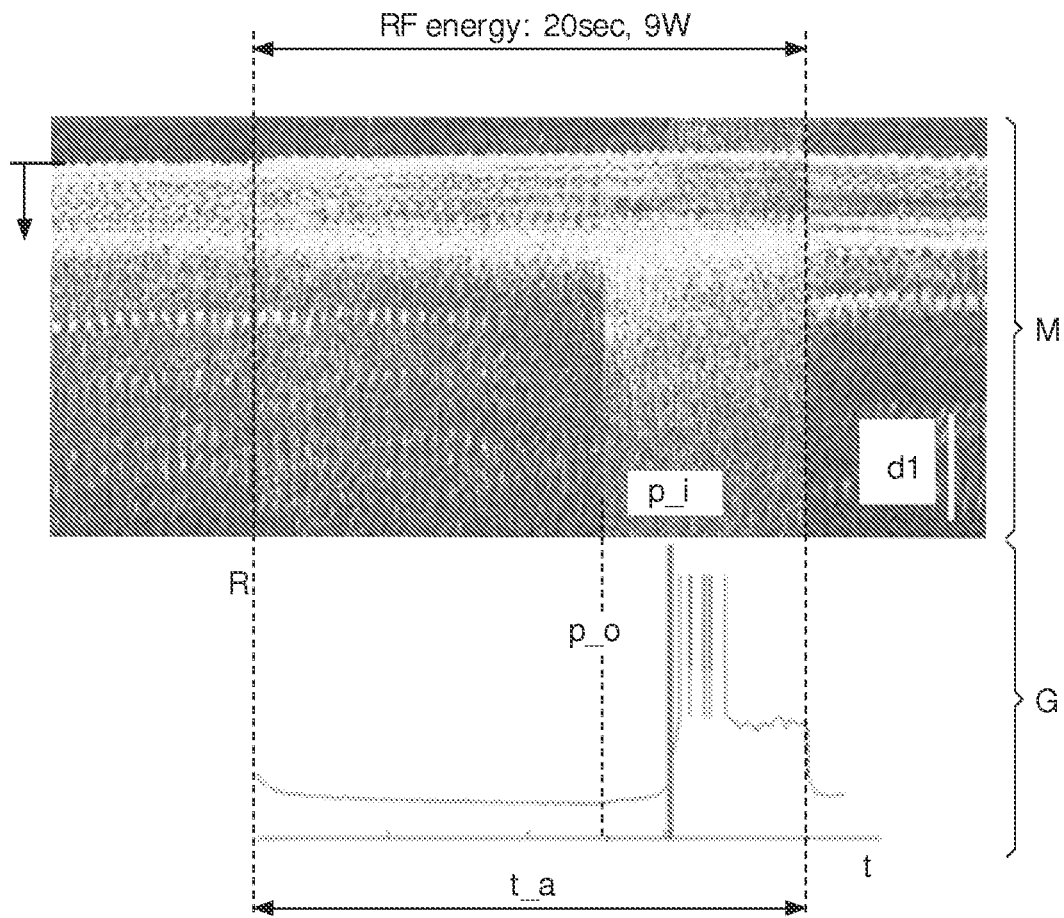
FIG. 4 shows experimental data from an open-chest sheep model according to an embodiment of the invention.

FIG. 4 shows experimental data from an open-chest sheep model. Radio frequency energy was delivered epicardially to create lesions that were simultaneously monitored with ultrasound and electrical impedance change. Tissue pops were deliberately induced and US data was compared with impedance data. The presence of pops was independently signaled by the physician that performed the ablation and who had no access to the US or impedance data. In clinical practice, loud pops are audible even through the chest of the patient, such as the chest of a sheep. The figure shows the data obtained with a set of ultrasound measurements and corresponding impedance measurements of an epicardial ablation with an integrated ring catheter. The ultrasound measurements re visualized in a so-called M-mode image M. The graph G depicted shows a temporal development of the electrical impedance during the ablation process. The time t is shown on the bottom axis, and the graph G and the M-mode image M share this time axis. The RF energy dissipated per time interval is 9 watt during the 20 second period denoted by t_a. The tissue depth in the M-mode image M is denoted by d_t. The absolute scale of the M-mode image is indicated by the scale bar denoted by d1, the scale bar corresponds to 1 millimeter. The vertical axis R in the graph G corresponds to electrical impedance measured in Ohm. Electrical impedance is measured between the ablation electrode and a ground electrode, which is at the back of the subject being investigated, such as on the back of a person or an animal, so the electrical impedance is measured across the tissue. Typically, the electrical impedance measured at the catheter tip increases in case of pops. The solid line denoted p_i indicates the incidence of a tissue pop, the dashed line denoted d_o indicate the onset of changes in ultrasound that precede the pops. The figure shows that changes in the ultrasound measurements before tissue pops preceded changes in impedance by several seconds. From the ultrasound M-mode image recorded during the ablation procedure, the change of ultrasound signal could be associated with bubble formation, before the physician signaled the pop.

Figure 5:
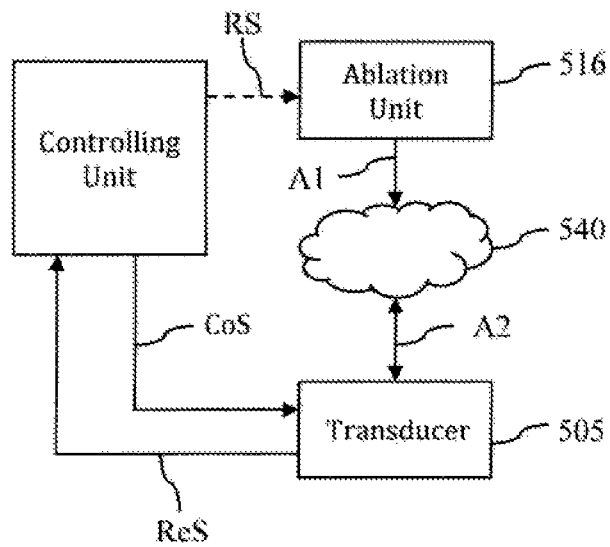
FIG. 5 shows a schematic drawing of a system according to an embodiment of the invention.

FIG. 5 shows a schematic drawing of a system according to an embodiment of the invention, comprising an ultrasound transducer 505, an ablation unit 516, a controlling unit (CTRL). Furthermore is shown an associated tissue 540. In the figure, the controlling unit sends and receives respectively a control signal (CoS) and a response signal (ReS) to and from the ultrasound transducer 505, the response signal being indicative of the presence of one or more bubbles within said associated tissue. The controlling unit calculates a predictor value, where the predictor value relates to a risk of impending tissue damage due to a rapid release of bubble energy, and sends a primary signal (RS) if the predictor value exceeds a threshold value. In the shown embodiment, the primary signal (RS) is sent to the ablation unit 516. In such embodiment, the primary signal (RS) might thus serve to decrease an ablation power, in order to decrease a risk of impending tissue damage due to a rapid release of bubble energy.

Figure 6:
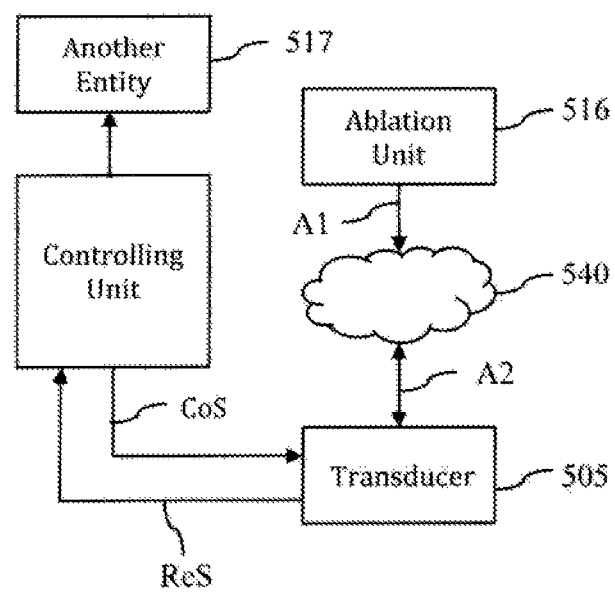
FIG. 6 shows another schematic drawing of a system according to an embodiment of the invention.

FIG. 6 shows another schematic drawing of a system according to an embodiment of the invention, similar to the embodiment shown in FIG. 5, except that the primary signal is sent to another entity 517 than the ablation unit. This other entity may be any entity, in particular it may be an entity controlling irrigation flow, an entity controlling a contact force applied between the interventional device and the associated tissue, or an entity controlling a position of the ablation unit.

Figure 7:
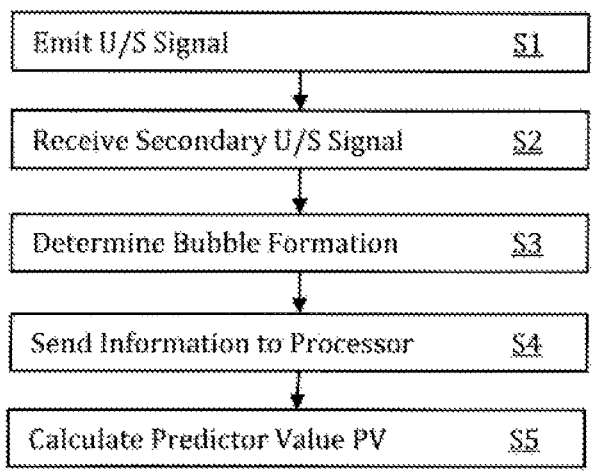
FIG. 7 is a flow-chart of a method according to an aspect of the invention.

FIG. 7 is a flow chart of a method for performing ablation according to an aspect of the present invention. Such a method comprises the steps of:

emitting S1 a primary ultrasonic signal into a tissue, and receiving S2 a secondary ultrasonic signal from within the tissue, and determining S3 if one or more bubbles are formed within the tissue, based upon information derived from the secondary ultrasonic signal, and sending S4 the information derived from the secondary ultrasonic signal to a processor, and calculating S5 a predictor value based on information derived from the secondary ultrasonic signal, where the predictor value relates to a risk of impending tissue damage due to a rapid release of bubble energy.

The steps S3 and S5 are carried out using the insight that generally the tissue pop is preceded by a sudden intensity increase from the ultrasound image. In particular embodiments image analysis based on different features might be applied to one or more images based on the ultrasound measurements in order to identify a relevant intensity increase, including check if a sudden significant gradient exists in the correlation map. This change should be consistent within a certain depth range (therefore different from noises), or monitor the histogram of one or more current lines in an M-mode image (also known as A-lines), check if there is a significant change in the graylevel distribution as compared to the previous A-line(s). Various distance metrics can be applied to compare the histograms such as correlation, Chi-Square, Bhattacharyya distance, etc. This approach might be varied so as to include that the histogram (distribution) doesn't have to be performed over the whole A-line. The A-line can be segmented into small segments and the histograms of these small segments can be checked.

as an alternative to the direct comparison of distributions, the mean, variance or higher order moments can be used to check the difference in histograms, or statistical features for texture characterization, such as entropy or texture parameter estimated from autoregressive models. These features can be used as alternatives for detecting the texture change when the tissue pop happens.

Along a single A-line, there is little variation in intensity (or intensity distribution) along the depth.

Figure 8:
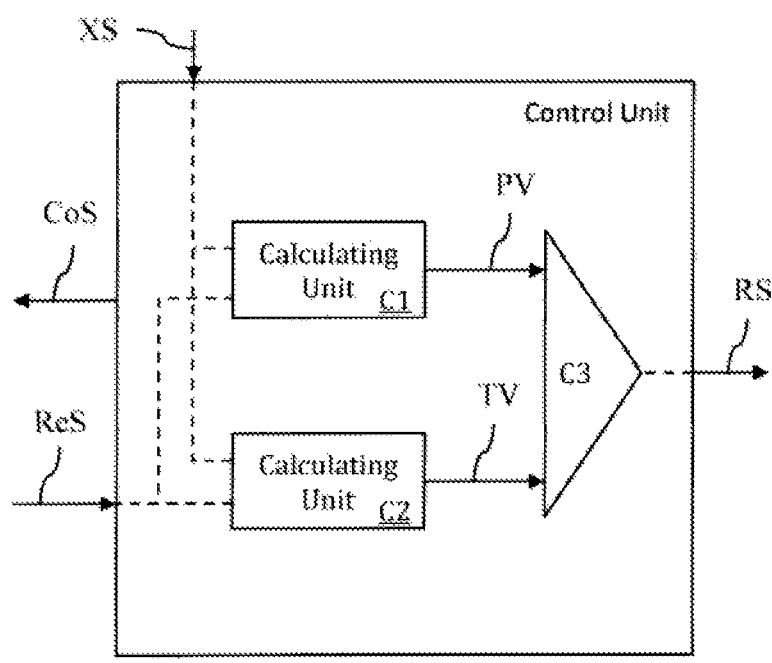
FIG. 8 shows a diagrammatic depiction of a controlling unit according to an embodiment of the invention.

FIG. 8 shows a diagrammatic depiction of a controlling unit (CTRL) according to an embodiment of the invention, wherein the controlling unit (CTRL) sends a control signal (CoS), such as a control signal for controlling an ultrasound transducer (not shown), and receives a response signal (ReS), such as a signal received from an ultrasound transducer, such as a signal representative of the a measured ultrasonic signal incident on the ultrasound transducer. In the shown embodiment, the controlling unit (CTRL) also receives an extra signal (XS) which may be any of a number of signals, such as a signal representative of a temperature, a flow of irrigation, or a contact force between the interventional device and a tissue. The controlling unit (CTRL) in this embodiment uses a first calculating unit (C1) and a second calculating unit (C2), which both receive both the response signal (ReS) and the extra signal (XS) to calculate respectively a predictor value (PV) and a threshold value (TV). In some embodiments, the first calculating unit (C1) and the second calculating unit (C2) also receive the control signal (CoS). A third calculation unit (C3) compares the predictor value (PV) with the threshold value (TV) and may output a primary signal (RS) which may also be output by the controlling unit if the predictor value (PV) exceeds the threshold value (TV).

To sum up, the present invention relates to a system (100) for combined ablation and ultrasound imaging of associated tissue (40), which is particularly useful for use in an ablation process. The system comprises an interventional device (20) with an ultrasound transducer and an ablation unit. During an ablation process, the interventional device (20) can be applied for both ablation and imaging of the tissue (40) subject to the ablation. A controlling unit (CTRL) is further comprised within the system, and arranged to calculate a predictor value based on one or more signals from the ultrasound transducer, where the predictor value relates to a risk of impending tissue damage due to a rapid release of bubble energy. According to a specific embodiment, a primary signal is sent if the predictor value exceeds a threshold value, so that proper measures can be taken.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A system (100) for combined ablation and ultrasound imaging of associated tissue (40, 540), the system comprising
an interventional device (20), the interventional device comprising,
an ultrasound transducer (5, 505), and
an ablation unit (15, 516), and
a controlling unit (CTRL) being operably connected to the interventional device (20), the controlling unit (CTRL) being arranged to
send a control signal (CoS) to the ultrasound transducer (5, 505),
receive a response signal (ReS) from the ultrasound transducer, the response signal (ReS) being indicative of the presence of one or more bubbles within said associated tissue (40, 540), and
calculate a predictor value (PV), where the predictor value (PV) relates to a risk of an impending tissue damage due to a rapid release of a bubble energy,
wherein the controlling unit ((CTRL) is further arranged to send a primary signal (RS) if the predictor value (PV) exceeds a threshold value, and
wherein the primary signal (RS) is arranged to control an ablation parameter while ablation is continued.

2. A system (100) for combined ablation and ultrasound imaging of associated tissue according to claim 1, wherein the threshold value (TV) is a function of any one of: a power dissipated in the associated tissue (40, 540), the previous history of the response signal, a measured contact force between the interventional device and the associated tissue (40, 540), an electrical impedance of the associated tissue (40, 540), a structure of the associated tissue (40, 540), a duration of the ablation, the ability of the associated tissue to exchange heat with the surroundings, a temperature of the associated tissue (40, 540), the temperature of the ablation electrode, and the irrigation flow rate at the electrode tip.

3. A system (100) for combined ablation and ultrasound imaging of associated tissue (40, 540) according to claim 2, wherein the controlling unit (CTRL) is arranged to vary the primary signal (RS) depending on the value of the predictor value (PV).

4. A system (100) for combined ablation and ultrasound imaging of associated tissue (40, 540) according to claim 3, wherein the controlling unit (CTRL) is arranged to form part of a feedback circuit.

5. A system (100) for combined ablation and ultrasound imaging of associated tissue (40, 540) according to claim 3, wherein the ultrasound transducer (5, 505) is disposed behind or in an irrigation hole (21) of the interventional device (20), so as to allow an irrigation fluid to flow out of the irrigation hole (21), and so as to allow transmitting and/or receiving an ultrasonic signal (A2) through the irrigation hole (21).

6. A system (100) for combined ablation and ultrasound imaging of associated tissue (40, 540) according to claim 3, wherein the ablation unit (15, 516) comprises any one of: a heating element, a radio frequency electrode, an ultrasound transducer, and a laser.

7. A system (100) for combined ablation and ultrasound imaging of associated tissue (40, 540) according to claim 3, the system comprising any one of: an electrode capable of serving as an electrode for measuring electrical impedance, a force sensor capable of measuring a contact force applied between the interventional device and the associated tissue (40, 540), and a temperature sensor and localization sensor.

8. A system (100) for combined ablation and ultrasound imaging of associated tissue (40, 540) according to claim 3, wherein the primary signal (RS) is controlling any one of: the ablation unit (15, 516), an irrigation flow, a contact force applied between the interventional device and the associated tissue (40, 540), and a position of the ablation unit.

9. The system according to claim 3, wherein the ablation parameter controlled based on the primary signal is an irrigation flow.

10. The system according to claim 3, wherein the ablation parameter controlled based on the primary signal is a contact pressure between the interventional device and the associated tissue.

11. A method for assessing a risk of impending tissue damage due to a rapid release of a bubble energy, the method comprising
emitting (S1) a primary ultrasonic signal into a tissue, and
receiving (S2) a secondary ultrasonic signal from within the tissue, and determining (S3) if one or more bubbles are formed within the tissue, based upon information derived from the secondary ultrasonic signal, and sending (S4) the information derived from the secondary ultrasonic signal to a processor, and calculating (S5) a predictor value (PV) based on information derived from the secondary ultrasonic signal, where the predictor value (PV) relates to the risk of impending tissue damage due to the rapid release of the bubble energy, sending a primary signal (RS) if the predictor value (PV) exceeds a threshold value, and controlling an ablation parameter while ablation is continued.

12. The method according to claim 11, wherein the ablation parameter controlled based on the primary signal is an irrigation flow.

13. The method according to claim 11, wherein the ablation parameter controlled based on the primary signal is a contact pressure between the interventional device and the associated tissue.

14. A computer program product comprising a non-transitory, computer readable storage medium being adapted to enable a computer system comprising at least one computer having data storage means associated therewith to operate a processor arranged for receiving information derived from an ultrasonic signal indicative of the presence of one or more bubbles within associated tissue, calculating a predictor value (PV) based on information derived from the secondary ultrasonic signal, where the predictor value relates to a risk of an impending tissue damage due to a rapid release of a bubble energy sending a primary signal (RS) if the predictor value (PV) exceeds a threshold value, and controlling an ablation parameter while ablation is continued based on the primary signal.

15. The computer program product according to claim 14, wherein the ablation parameter controlled based on the primary signal is an irrigation flow.

16. The computer program product according to claim 14, wherein the ablation parameter controlled based on the primary signal is a contact pressure between the interventional device and the associated tissue.

* * * * *